(12) United States Patent
Baranton et al.

(10) Patent No.: US 10,036,902 B2
(45) Date of Patent: Jul. 31, 2018

(54) METHOD OF DETERMINING AT LEAST ONE BEHAVIOURAL PARAMETER

(71) Applicant: ESSILOR INTERNATIONAL (COMPAGNIE GENERALE D'OPTIQUE), Charenton-le-Pont (FR)

(72) Inventors: Konogan Baranton, Charenton-le-Pont (FR); Guilhem Escalier, Charenton-le-Pont (FR); Sebastien Gayat, Charenton-le-Pont (FR)

(73) Assignee: ESSILOR INTERNATIONAL (COMPAGNIE GENERALE D'OPTIQUE), Charenton-le-Pont (FR)

( * ) Notice: Subject to any disclaimer, the term of this patent is extended or adjusted under 35 U.S.C. 154(b) by 0 days.

(21) Appl. No.: 15/312,473

(22) PCT Filed: May 19, 2015

(86) PCT No.: PCT/FR2015/051316
§ 371 (c)(1),
(2) Date: Nov. 18, 2016

(87) PCT Pub. No.: WO2015/177461
PCT Pub. Date: Nov. 26, 2015

(65) Prior Publication Data
US 2017/0115513 A1    Apr. 27, 2017

(30) Foreign Application Priority Data
May 20, 2014    (FR) ...................................... 14 54548

(51) Int. Cl.
*A61B 5/16*    (2006.01)
*G02C 13/00*    (2006.01)
*A61B 5/107*    (2006.01)

(52) U.S. Cl.
CPC .......... *G02C 13/005* (2013.01); *A61B 5/1079* (2013.01); *A61B 5/16* (2013.01)

(58) Field of Classification Search
CPC ..... A61B 3/111; A61B 5/1114; A61B 5/6814; A61B 5/1176; A61B 5/16; A61B 5/6821
(Continued)

(56) References Cited

U.S. PATENT DOCUMENTS

| 2010/0118123 A1 | 5/2010 | Freedman et al. |
| 2010/0128220 A1 | 5/2010 | Chauveau |

(Continued)

FOREIGN PATENT DOCUMENTS

| FR | 2 914 173 A1 | 10/2008 |
| FR | 2 974 722 A1 | 11/2012 |

(Continued)

OTHER PUBLICATIONS

International Search Report, dated Jul. 29, 2015, from corresponding PCT Application.

*Primary Examiner* — Hung Dang
(74) *Attorney, Agent, or Firm* — Young & Thompson

(57) ABSTRACT

A method of determining at least one behavioral parameter of a wearer for designing an ophthalmic eyeglass lens includes: a) acquiring a first data set from a first representation of the head of the wearer in three dimensions; b) determining the relative position in space of at least three particular points of the head based on the data set; c) acquiring a second data set from a second representation of the head in a natural posture, including at least one image of each of the three particular points; d) identifying the image of each of the particular points from step b) on the representation of step c); e) deducing information relating to the position and/or to the orientation of the head of the wearer during the determination of the second representation from (Continued)

Figure 1:
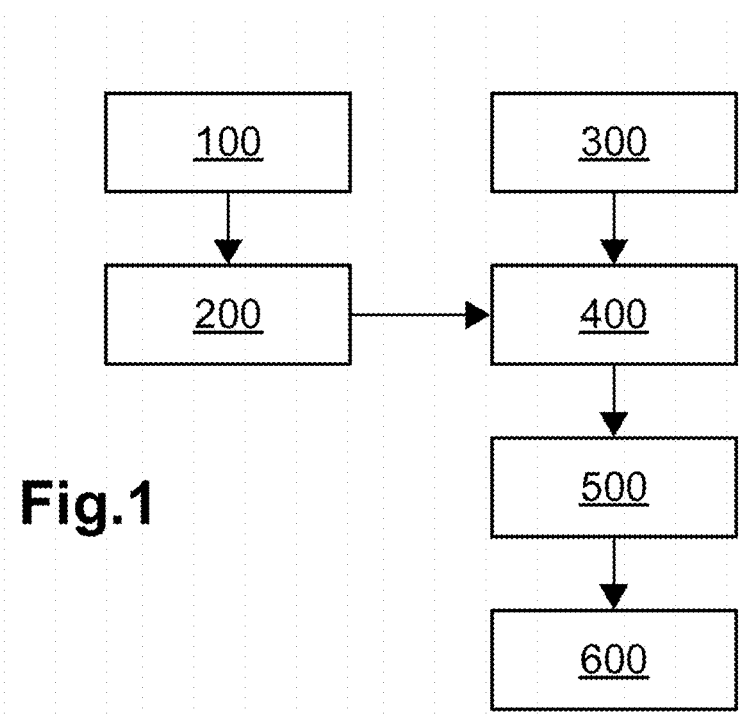

this identification; and f) determining the behavioral parameter of the wearer based on the information from step e).

23 Claims, 1 Drawing Sheet

(58) Field of Classification Search
USPC .......................................... 351/204, 246, 41
See application file for complete search history.

(56) References Cited

U.S. PATENT DOCUMENTS

| | | |
|---|---|---|
| 2014/0293219 A1 | 10/2014 | Haddadi et al. |
| 2015/0049306 A1* | 2/2015 | Haddadi ................ A61B 3/11 |
| | | 351/206 |
| 2015/0109577 A1 | 4/2015 | Haddadi et al. |
| 2015/0198822 A1 | 7/2015 | Divo et al. |

FOREIGN PATENT DOCUMENTS

| | | |
|---|---|---|
| FR | 2 987 918 A1 | 9/2013 |
| WO | 02/09025 A1 | 1/2002 |
| WO | 2014/016502 A1 | 1/2014 |

\* cited by examiner

METHOD OF DETERMINING AT LEAST ONE BEHAVIOURAL PARAMETER

TECHNICAL FIELD OF THE INVENTION

The present invention generally relates to a method for determining at least one behavioral parameter of a wearer with a view to designing an ophthalmic lens for a spectacle frame of this wearer.

PRIOR ART

The design and manufacture of an ophthalmic lens suitable for a wearer and for a chosen spectacle frame presently requires one or more measurements to be taken at an opticians.

These measurements are often biased by the unnatural behavior of the wearer at the opticians. Specifically, the environment of the shop of the optician is often very different from the usual living environment of the wearer and therefore the usual conditions of use. Furthermore, the measurements carried out at the opticians must be carried out very rapidly.

Measurements carried out at an opticians are therefore imprecise because of the unnatural conditions under which the measurements are taken.

Systems for taking measurements outside of opticians shops and allowing pairs of spectacles to be bought over the Internet are also known.

These systems thus allow measurements to be taken under conditions that are closer to those of the everyday life of the wearer.

However, these known systems can only measure geometrico-morphological parameters such as the value of interpupillary distance. These known systems do not allow behavioral parameters of the wearer, i.e. parameters related to the visual behavior of the wearer, such as for example reading distance or the eye-head coefficient, to be determined.

The determination of these behavioral parameters is more complex and the associated measurements are presently only doable at an opticians.

SUBJECT OF THE INVENTION

In order to remedy the aforementioned drawbacks of the prior art, the present invention provides a new method for determining at least one behavioral parameter of a wearer, by virtue of which it is possible to precisely determine this parameter under conditions that are natural for the wearer.

More particularly, according to the invention a method is provided for determining at least one behavioral parameter of a wearer with a view to designing an ophthalmic lens for a spectacle frame of this wearer, including the following steps:

a) acquiring a first dataset corresponding to a first representation of the head of the wearer in three dimensions, b) determining, from this dataset, the relative position in space of at least three particular points of the head of the wearer, c) acquiring a second dataset corresponding to a second representation of the head of the wearer in a natural posture, comprising at least one image of each of the three particular points of the head of the wearer, d) identifying, in said second representation of step b), the image of each of said particular points of the head of the wearer the relative positions in space of which were determined in step b), e) deducing from this identification information relating to the position and/or orientation of the head of the wearer during the determination of said second representation, f) determining, from the information deduced in step e) (and possibly from said second representation), said behavioral parameter of the wearer.

It is thus possible to take into account the position and/or orientation of the head of the wearer in this natural posture during the determination of the behavioral parameter.

An exemplary behavioral parameter is the cephalic carriage of the wearer (for example defined by a lowering angle and/or a roll angle). Other examples are given in the following description.

Each dataset may comprise data stored in various files. One dataset may for example contain the data of a file corresponding to an image and meta data stored in another file.

The following are other nonlimiting and advantageous features of the method according to the invention:

in step a), at least one three-dimensional image of the head of the wearer is acquired by virtue of a first device for capturing three-dimensional images, this three-dimensional image then constituting said first representation of the head of the wearer;

in step a), a series of three-dimensional first images of the head of the wearer is acquired and, in step b), said particular points are determined, by virtue of a statistical analysis, depending on the points of the head of the wearer the relative positions of which are the most stable in the series of three-dimensional first images;

in step a), a series of two-dimensional first images of the head of the wearer in various cephalic postures is acquired using a first device for capturing two-dimensional images, this series of first images constituting said first representation of the head of the wearer, and, for each captured first image, the corresponding position and/or orientation of the head of the wearer with respect to the first image-capturing device is determined;

in step c), at least one two-dimensional second image of the head of the wearer is captured using a second image-capturing device that is distinct from the first image-capturing device, said at least one two-dimensional second image of the head of the wearer constituting said second representation of the head of the wearer, and, in step e), that first image of said series of first images which is closest said second image is associated with the second image captured in step c) and the position and/or orientation of the head of the wearer with respect to said second image-capturing device during the capture of said second image is identified with the position and/or orientation of the head of the wearer during the capture of this closest first image;

in step a) and/or in step c), said dataset comprising said first and second representations of the head of the wearer, which representations are determined beforehand, is stored;

in step c), the second representation of the head of the wearer is determined during one or more habitual activities of the wearer, in his environment;

the habitual activity of the wearer is one of the following activities:
reading from various media,
working at a desk,
driving an automobile,
practicing a sport,
cooking,
playing on a games console,
resting seated,
watching the television,
playing a musical instrument;

in step c), at least one two-dimensional second image of the head of the wearer is captured using a second image-capturing device, said at least one two-dimensional second image of the head of the wearer constituting said second representation of the head of the wearer;

in step c), at least one three-dimensional second image of the head of the wearer is acquired by virtue of a second device for capturing three-dimensional images, said three-dimensional second image constituting said second representation of the head of the wearer;

in step c), a series of two- or three-dimensional second images of the head of the wearer is acquired and, in step f), said behavioral parameter of the wearer is determined depending on a statistical treatment of said second images of this series;

in step c), the series of second images of the head of the wearer being acquired while the wearer is fixating his gaze on a visual target, the position of this visual target with respect to the second image-capturing device is determined during the capture of each second image;

a step of calibrating the second device for capturing two- or three-dimensional images is carried out, in which step an image of a dedicated standard object is captured with this second image-capturing device;

the position and/or orientation in space of said second image-capturing device is determined during the capture of said two- or three-dimensional second image, and information relating to the position and/or orientation of the head of the wearer in space during the capture of this second image is determined therefrom;

in a step prior to step d), each two- or three-dimensional second image captured in step b) is transmitted to at least one information-processing server and stored in correspondence with an identifier of the wearer;

each captured second image transmitted to the server is associated with those particular points of the head of the wearer which were determined in step a), said image being stored on the server in correspondence with said identifier of the wearer;

in step e), the position and/or orientation of the head of the wearer during the determination of said second representation, are/is determined computationally as being the position and/or orientation of the head of the wearer for which the three particular points of the head of the wearer have the coordinates of the images of the three particular points identified in said second representation;

the behavioral parameter determined in step f) is one of the following:
reading distance,
ratio of the angular movements of the eye and head,
static or dynamic posture adopted for the habitual activity in question,
ergorama associating with each direction of the gaze the distance between the eye and the point looked at,
variability in the aforementioned behavioral parameters,
position of the spectacle frame of the wearer on his face;

in step a), a first representation of the head of the wearer is acquired by a person specialized in optometry, other than the wearer, and/or using a device dedicated to optometry, whereas, in step c), a second representation of the head of the wearer is acquired under the responsibility of the wearer himself, without intervention of a person specialized in optometry and/or using a commonplace device; and, in step b), the three particular points of the head of the wearer are associated with an accessory worn on the head of the wearer, and their relative positions in a frame of reference associated with this accessory are known.

DETAILED DESCRIPTION OF ONE EXEMPLARY EMBODIMENT

The description which follows with regard to the appended drawings, given by way of non-limiting examples, will clearly elucidate the essence of the invention and the manner in which it may be carried out.

Figure 2:
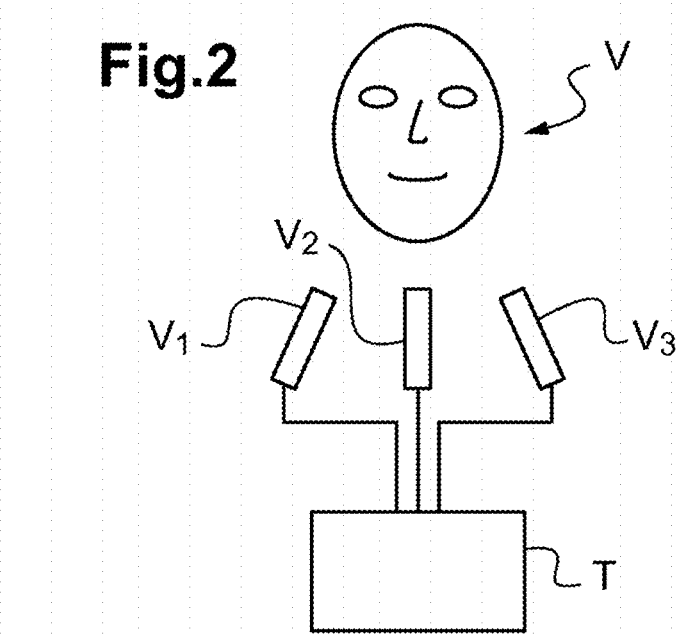

In the appended drawings:

FIG. 1 is a block diagram schematically showing the method according to the invention, FIG. 2 schematically shows one possible implementation of step a) of the method.

The invention relates to a method for determining at least one behavioral parameter of a wearer with a view to designing an ophthalmic lens for a spectacle frame of this wearer.

This behavioral parameter may especially be one of the following:
reading distance, i.e. the distance separating the eyes of the wearer from the medium bearing the read text or the visual target fixated by the gaze of the wearer,
the ratio of the angular movements of the eye and head, i.e. the ratio of the amplitude of the movement of an eye of the wearer in a determined direction to the maximum amplitude of the movement of this eye during the reading task, also called eye-head coefficient,
the posture of the head and/or of the body adopted for the habitual activity in question, i.e. the position and/or orientation of the head and/or the body in a frame of reference associated with a visual target fixated by the gaze of the wearer,
the ergorama associating with each direction of the gaze the distance between the eye and the point looked at,
the variability in one of the aforementioned parameters,
the position of the spectacle frame of the wearer on his face.

According to the invention, the method includes the following steps:

a) acquiring a first dataset corresponding to a first representation of the head of the wearer in three dimensions (block 100 in FIG. 1), b) determining, from this dataset, the relative position in space of at least three particular points of the head of the wearer (block 200 in FIG. 1), c) acquiring a second dataset corresponding to a second representation of the head of the wearer in a natural posture, comprising at least one image of each of the three particular points of the head of the wearer (block 300 in FIG. 1), d) identifying, in said second representation of step b), the image of each of said particular points of the head of the wearer the relative positions in space of which were determined in step b) (block 400 in FIG. 1), e) deducing from this identification information relating to the position and/or orientation of the head of the wearer during the determination of said second representation (block 500 in FIG. 1), f) determining, from said second representation and the information deduced in step e), said behavioral parameter of the wearer (block 600 in FIG. 1).

Preferably, in step a), a first representation of the head of the wearer is acquired by a person specialized in optometry, other than the wearer, and/or using a device dedicated to optometry, whereas, in step c), a second representation of the head of the wearer is acquired under the responsibility of the wearer himself, without intervention of a person specialized in optometry and/or using a commonplace device.

Thus, it is possible to decouple the determination of the first representation and that of the second representation of the head of the wearer.

The first representation of the head of the wearer may be determined at an opticians, with the dedicated means possessed thereby, and under the particular conditions associated with the workplace of the optician, especially in terms of the positioning of the wearer, lighting, measuring devices and the short time dedicated to the measurement. In contrast, the second representation of the head of the wearer is preferably determined by the wearer himself, in his environment, using commonly available measuring devices such as a camera, a video camera or a webcam, it then being possible for him to devote much more time thereto than is dedicated to this determination at an opticians.

Furthermore, in the case where the determination of each representation comprises acquiring one or more images with an image-capturing device, it will be understood that the first image-capturing device associated with the acquisition of the first representation and the second image-capturing device associated with the acquisition of the second representation are distinct.

Likewise, when one of these two steps comprises simply retrieving a dataset corresponding to the first and/or second representation of the head of the wearer, each dataset preferably contains the digital data corresponding to one or more two- or three-dimensional images captured beforehand with a first and second image-capturing device that are distinct.

Thus, in practice, according to one preferred possible implementation of the invention, the steps of the method are on the whole carried out in the following way.

The wearer goes to an opticians and selects a spectacle frame. The wearer may then choose ophthalmic lenses without personalization.

Step a) of taking three-dimensional measurements is preferably carried out there and then, for example using stereoscopic video cameras or a 3-D scanner, for example. The optician may also retrieve a pre-existing dataset, for example corresponding to measurements taken beforehand. This dataset may also optionally be transmitted to the wearer.

A three-dimensional model of the head of the wearer is produced in step b), either at the opticians, or in a remote computational center after transmission of the acquired data.

In order to personalize the ophthalmic lenses intended to be fitted in the frame chosen by the wearer, the optician asks the wearer to take photos or videos of himself in various everyday situations.

For this purpose, the wearer uses mass-market measuring means such as a camera, a movie camera, a video camera integrated into a smart phone, a tablet or a TV screen, a WebCam, a Kinect module, etc.

Preferably, the wearer calibrates the measuring means by imaging a dedicated standard.

He takes one or more series of day-to-day measurements. The wearer takes photos of himself in everyday situations: at work, reading, while he is relaxing (watching TV, playing games, etc.), or during particular activities (cooking, sport, music, driving, etc.).

The series of measurements may be repeated a plurality of times.

All of the acquired data are transmitted for processing to the optician or to a remote computational center.

The association of the three-dimensional model of the head of the wearer with the data collected by the wearer during his day-to-day routine allow them to be treated statistically in order to extract therefrom behavioral parameters such as:
  fixation distance
  ergorama
  current position of the frame.

These behavioral parameters are used to personalize the ophthalmic lenses intended for the wearer. They allow a standard ophthalmic lens to be modified in order to make it match as best as possible the needs of the wearer. It is also possible to weight behavioral parameters already determined at the opticians.

The various steps of the method according to the invention will now be described in detail.

Step a)

Thus, in practice, step a) is preferably carried out by a person specialized in optometry, for example, at an opticians, or in a kiosk equipped with a device dedicated to optometry, and connected to an information-processing device.

The aim of step a) is to take measurements allowing a three-dimensional model of at least the head of the wearer to be produced. A partial or complete three-dimensional model of the body of the wearer may also be determined. For example, a model of the chest of the wearer may be produced from the determination of the position of two particular points of the chest, namely the acromions called the manubrium and the xyphoid apophysis.

The manubrium designates the top portion of the sternum, to which the clavicles are hinged. The xyphoid apophysis is a bony or cartilaginous structure that is located at the bottom end of the sternum. It is thus possible to determine the position of the head with respect to the chest.

This three-dimensional model is produced in step b), as explained below.

This measuring step may be carried out in various ways.

According to a first embodiment of step a), at least one three-dimensional image of the head of the wearer is acquired by virtue of a first device for capturing three-dimensional images, this three-dimensional image then constituting said first representation of the head of the wearer.

The first device for capturing three-dimensional images is for example a three-dimensional scanner, or a device for capturing stereoscopic images comprising at least two apparatuses for capturing two-dimensional images simultaneously recording two two-dimensional images of the head of the wearer in two image-capturing planes that are oriented differently with respect to the head of the wearer. In this case, each three-dimensional image comprises at least two two-dimensional images and information relating to the relative position of the two image-capturing apparatuses.

The first device for capturing three-dimensional images may especially be based on a structured light technique.

This first capturing device then comprises means for projecting structured light, for example including a pattern such as a moiré pattern, onto the head of the individual while the image-capturing means record one or more two-dimensional images of the head of the individual.

Since the pattern is known, processing of these images allows the three-dimensional representation to be determined.

It is possible to envision, preferably, acquiring a series of three-dimensional first images, this series then constituting the first representation of the head of the wearer.

The wearer is here preferably bare-headed, i.e. his head is devoid of optical equipment such as a spectacle frame or ophthalmic lens.

In practice, to implement this step a), the device shown in FIG. 2 may be used.

FIG. 2 shows a system for taking measurements of the face V of the head of the wearer. This system especially comprises n video cameras $V_i$ (n=3 in the embodiment shown in FIG. 1) and a processing device T connected to each of the n video cameras $V_i$.

The processing device T is for example based on a microprocessor-based architecture. In such a system, the microprocessor executes the instructions of a program stored in a memory associated with the microprocessor in order to implement processing methods such as those presented below.

The processing device for example furthermore comprises a screen, a user interface (such as a keyboard or a mouse) and an electronic storing apparatus such as a hard disk. These components are connected to the microprocessor and are controlled by the microprocessor by way of the execution of dedicated instructions by the microprocessor.

The video cameras $V_i$ are calibrated using a standard and with respect to one another, this meaning that, in an imaging plane in which the wearer will position his face, the n video cameras $V_i$ acquire images representing the same zone of the face of the wearer.

Each video camera $V_i$ acquires a sequence of two-dimensional images $I_i(t_1), \ldots, I_i(t_m)$ taken respectively at times $t_1, \ldots, t_m$.

According to a second embodiment of step a), a series of two-dimensional first images of the head of the wearer in various cephalic postures is acquired using a first device for capturing two-dimensional images, this series of two-dimensional first images constituting said first representation of the head of the wearer, and, for each captured two-dimensional first image, the corresponding position and/or orientation of the head of the wearer with respect to the first image-capturing device is determined.

In this case it is a question of a series of non-stereoscopic first images: the first image-capturing device captures, at a given time t, a single two-dimensional image of the head of the wearer.

Specifically, it is possible to envision placing on the head of the wearer an accessory having set geometric characteristics. It may for example be a question of the chosen spectacle frame or of a frame other than that chosen, the latter preferably having dimensions larger than that chosen so that the gaze of the wearer is not constrained by the edges of the frame.

The frame is preferably equipped with a pinpointing system intended to allow the position of the head of the wearer in space to be determined from a captured image of the head of the wearer equipped with the locating system. This pinpointing system is described in detail in document FR2914173, page 7, line 5 to page 10, line 8. It will therefore not be described in more detail here.

This pinpointing system has predetermined geometric characteristics, which allow, from a captured image of the head of the wearer, in which image this locating system appears, the position and the orientation of the head of the wearer in space to be determined in a frame of reference associated with the image-capturing device. This pinpointing system therefore allows the position and orientation of a frame of reference associated with the head of the wearer to be determined in the frame of reference associated with the image-capturing device.

The head of the wearer may be directly equipped with the pinpointing system.

According to a third embodiment of step a), said dataset comprising said first representation of the head of the wearer, which representation is determined beforehand, is stored. Step a) then does not comprise an image-capturing step. It is a question of retrieving a digital file that has been determined beforehand.

This dataset may especially contain data corresponding to a three-dimensional image, said data having been captured beforehand (for example using a three-dimensional scanner or a device for capturing stereoscopic images), or to a series of two-dimensional images captured beforehand. In the latter case, the set also contains in association with the data corresponding to each two-dimensional image, information relating to the position and/or orientation of the head of the wearer with respect to the first image-capturing device during the capture of this image.

Step b)

From this dataset, the relative position in space of at least three particular points of the head of the wearer is determined.

Preferably, the relative position in space of at least four particular points of the head of the wearer is determined.

This step corresponds to the establishment of a three-dimensional frame of reference associated with the head of the wearer. This three-dimensional frame of reference is an absolute frame of reference, in space, or a frame of reference associated with the environment of the wearer, and is not associated with the first image-capturing device.

Said three particular points of the head of the wearer may be particular points located directly on the head of the wearer.

It is then preferably a question of predefined morphological points of the face, for example the commissures of the lips, the end of the wings of the nose, the corners of each eye of the wearer (i.e. the internal and external canthi of the eyes), the eyebrows or the teeth of the upper jaw.

Whatever the embodiment of step a), the dataset established in step a) is stored for this purpose in an information-processing server, which may optionally comprise the processing device T described above. The information-processing server may be located at the opticians or remotely in a remote computational center. In the latter case, the dataset is transmitted to the remote information-processing server.

In practice, in step b), a step is carried out of recognizing the image of each of these particular points in each image captured in step a) or in the dataset retrieved in step a).

In particular, in the case where, in step a), a series of three-dimensional first images of the head of the wearer is acquired, in step b), said particular points are then determined, by virtue of a statistical analysis, depending on the points of the head of the wearer the relative positions of which are the most stable in the series of three-dimensional first images. This statistical analysis may especially comprise determining a statistical model of the head of the wearer.

For example, in the case where, in step a), a three-dimensional image of the head of the wearer is captured by virtue of a device for capturing stereoscopic images, the following substeps may be implemented in step b). The information-processing server here comprises the processing device T described above. Each of the substeps described below is here implemented by the microprocessor of the processing device T, on the basis of instructions stored in a memory associated with the microprocessor; the data processed by the microprocessor (such as the images taken by the video cameras or the coordinates of the characteristic points in the various models) are also stored in this memory or stored by another means such as a hard disk. Any other implementing means known to those skilled in the art may also be envisioned. The data may for example be processed by a hypervisor of a cluster of virtualized servers.

In a first substep, in each image $I_i(t_j)$ a plurality of p characteristic points of the face shown in the image in question are determined. The p points determined in an image $I_i(t_j)$ as corresponding to the p characteristic points of the face are denoted $Q_{i,j}(1), \ldots, Q_{i,j}(p)$. The processing device then for example stores in memory the (two-dimensional) coordinates of each of the characteristic points in the image in question.

The characteristic points are for example determined using a facial recognition algorithm, here an "*Active Appearance Model*" algorithm (see for example on this subject the article "*Active appearance models*", by T. F. Cootes, G. J. Edwards, C. J. Taylor, in IEEE Transactions on Pattern Analysis and Machine Intelligence 23 (6): 681, 2011).

Next a second substep is carried out in which the characteristic points of each series of images $I_1(t_j), \ldots, I_n(t_j)$, i.e. of each set of n images taken by the n video cameras $V_i$ at a given time $t_j$, are associated in order to obtain, for each series of images, a three-dimensional model of the face, namely a set of locations of the characteristic points of the face, said locations being defined by three-dimensional coordinates.

More precisely, for each characteristic point k of the face and for each series of images $I_1(t_j), \ldots, I_n(t_j)$ (corresponding to the images taken at a time $t_j$), the coordinates of the points $Q_{1,j}(k), \ldots, Q_{n,j}(k)$ in these images are used to evaluate the three-dimensional coordinates of the point $P_k(t_j)$ at which the characteristic point k of the face is located at the time $t_j$, for example using an epipolar geometry (and by virtue of the aforementioned calibration of the video cameras $V_i$).

It will be noted here that, because the face of the wearer is movable and deformable, the three-dimensional model obtained (defined by the set of points $P_k(t_j)$ at a time $t_j$) a priori varies depending on the time $t_j$ in question.

Next, a third substep is carried out in which each three-dimensional model obtained in the preceding step is adjusted with respect to a reference model.

For example, the three-dimensional model associated with the time $t_1$ is used as a reference model in the first iteration of the third substep. As a variant, another three-dimensional model obtained in the second substep could be used as reference model in the first iteration of the third substep.

For each three-dimensional model (associated with the image captured at the time $t_j$), the adjusting step is here carried out by minimizing the Euclidean distance between the point cloud of the three-dimensional model in question and the point cloud of the reference three-dimensional model, by translation and rotation in the space of the point cloud of the three-dimensional model in question.

Thus, if the points of the reference model are denoted $R_1, \ldots, R_p$ (for the first iteration, as already indicated, the model associated with the time $t_1$ is used, namely $R_k=P_k(t_1)$ for k ranging from 1 to p), the transformation F (composed of a translation and a rotation) is therefore sought that minimizes the Euclidean distance between the point cloud $R_k$ of the reference model and the point cloud of the model in question after transformation, i.e. that minimizes:

$\Sigma_{k=1}^{p} d(F(P_k(t_j)), R_k)$, where d is the (Euclidean) distance between two points.

The points of the adjusted model (i.e. after adjustment) will be denoted $P'_k(t_j)$:

$$P'_k(t_j)=F(P_k(t_j)).$$

The points of the adjusted model (or, equivalently, of the transformation F) are for example determined by means of an iterative closest point (ICP) algorithm—on this subject see for example the article "*Comparing ICP Variants on Real-World Data Sets*" by F. Pomerleau, F. Colas, R. Siegwart and S. Magnenat in Autonomous Robots, 34(3), pages 133-148, April 2013.

A fourth substep of constructing a statistical model formed from a set of points $S_k$ is then carried out on the basis of the adjusted models, each of which is formed from the points $P'_k(t_j)$. More precisely, each point $S_k$ of the statistical model is constructed on the basis of the points $P'_k(t_1), \ldots, P'_k(t_m)$ at which a given characteristic point k of the face is located at the various times $t_1, \ldots, t_m$ of image capture.

For each characteristic point k of the face, the point $S_k$ of the statistical model is for example defined as the centroid of the corresponding points $P'_k(t_1), \ldots, P'_k(t_m)$ in the various adjusted models.

As a variant, aberrant points may be rejected: to define $S_k$, the centroid of the points $P'_k(t_j)$ is determined anew, but without taking into account points that are too distant from the first calculated centroid (the centroid calculated on the basis of the m points $P'_k(t_j)$), for example those points located at a distance from the first calculated centroid that is above a threshold. It is proposed here to use as threshold, in the distribution of the distances of the various points at the calculated first centroid, the mean plus two standard deviations.

As a variant, the point $S_k$ of the statistical model may be the centroid of the points $P'_k(t_1), \ldots, P'_k(t_m)$ weighted by a coefficient for example relating:
- to the residual error of the point after adjustment (i.e. the Euclidean distance between the point $P'_k(t_j)$ in question after adjustment and the associated reference point $R_k$);
- to an error coefficient determined during the recognition of the characteristic points of the face in the second substep (the recognition of certain points possibly being more or less certain depending on the position of the face).

Moreover, it is proposed here to use, in the statistical model, only the points $S_k$ for which the uncertainty is low. The sum of the mean and two times the standard deviation of the distribution formed from the distances between the point $S_k$ determined as indicated above and the various corresponding points $P'_k(t_j)$ of the adjusted models are for example used as a measure of the uncertainty (for each value of k).

Only the points $S_k$ for which this measure of uncertainty is lower than a predetermined threshold are used in the rest of the processing. If this condition does not allow three points to be selected, the three points having the smallest measure of uncertainty are used.

This allows the particular points that are most stable and most characteristic of the processed face to be selected and thus the robustness of the model to be increased, thus allowing the model to deliver a stable and precise metrological frame of reference.

As a variant, the user (for example an optician) could be allowed to choose (by interactive selection, for example by means of the screen and user interface of the processing device T) the points $S_k$ that are the most representative, or to give a weighting to each of the points $S_k$.

According to another variant, all the points $S_k$ could be used in the statistical model, each point $S_k$ being determined from the m corresponding points $P'_k(t_j)$ of the m adjusted models.

The statistical model obtained in the first iteration of the fourth substep may be used as a metrological frame of reference. However, it is also possible to minimize the adjusting errors as will be explained now.

In this case, in a subsequent fifth substep it is determined whether a new iteration of the third and fourth substeps is necessary. To do this, a merit function equal to the mean of the measures of uncertainty obtained for the set of points $S_k$ used in the fourth substep is for example calculated.

If it is determined in the fifth substep that a new iteration of the third and fourth substeps must be implemented (for example because the merit function just calculated is higher than a predefined threshold and because a predetermined number of iterations has not been reached), the method repeats the third substep this time using as reference model the statistical model obtained in the last iteration of the fourth substep. Therefore, the third substep is implemented using, for the points $S_k$ for which the uncertainty is low: $R_k = S_k$.

If it is determined in the fifth substep that a new iteration of the third and fourth substeps is not necessary (for example because the merit function just calculated is lower than or equal to the predefined threshold or because the predetermined number of iterations has been reached), it is possible to use the last statistical model obtained.

Thus, at least three particular points $S_k$ associated with the head of the wearer are determined from statistical analysis of the series of three-dimensional first images of the head of the wearer captured in step a), in the case of use of a first device for capturing stereoscopic images.

The particular points of the head of the wearer may also comprise particular points located indirectly on the head of the wearer.

It may then be a question, in the case where the head of the wearer is equipped with an accessory, of at least three points associated with this accessory.

In the latter case, the relative positions of these three particular points of the accessory are known, by construction, in a frame of reference associated with this accessory.

The three particular points of the accessory may then be more easily identified by an image recognition algorithm by taking into account the constraint existing by construction on the relative position of these three points. Specifically, these particular points are easily identifiable because they have very recognizable shape and contrast characteristics and because their relative positions are fixed.

Step c)

In practice, step c) is preferably carried out by the wearer, at home or in his usual environment—office, automobile, etc.—and using a commonplace image-capturing device.

The aim of step c) is to take a measurement while the wearer is in a natural posture, i.e. in an unconstrained posture.

Preferably, in step c), the second representation of the head of the wearer is determined during one or more habitual activities of the wearer, in his environment.

More precisely, the habitual activity of the wearer may especially be one of the following activities:
 reading from various media,
 working at a desk,
 driving an automobile,
 practicing a sport,
 cooking,
 playing on a games console,
 resting seated,
 watching the television,
 playing a musical instrument.

This measuring step may be carried out in various ways.

According to a first embodiment of step c), in step c), at least one three-dimensional second image of the head of the wearer is acquired by virtue of a second device for capturing three-dimensional images, which device is distinct from the first image-capturing device, said three-dimensional second image constituting said second representation of the head of the wearer.

The second device for capturing three-dimensional images is for example a three-dimensional scanner, or a device for capturing stereoscopic images comprising at least two apparatuses for capturing two-dimensional images simultaneously recording two two-dimensional images of the head of the wearer in two image-capturing planes that are oriented differently with respect to the head of the wearer. In this case, each three-dimensional image comprises at least two two-dimensional images and information relating to the relative position of the two image-capturing apparatuses.

This device may especially be a "Kinect", the operating principle of which is described in document US20100118123.

It is preferably possible to envision acquiring a plurality of three-dimensional images.

The wearer is here preferably bare-headed, i.e. his head is devoid of optical equipment such as a spectacle frame or ophthalmic lens.

According to a second embodiment of step c), at least one two-dimensional second image of the head of the wearer is captured using a second image-capturing device that is distinct from the first image-capturing device, said at least one two-dimensional second image of the head of the wearer constituting said second representation of the head of the wearer.

Preferably, according to a third embodiment of step c), a series of two-dimensional second images of the head of the wearer in various cephalic postures is acquired using a second device for capturing two-dimensional images, this series of second images constituting said second representation of the head of the wearer, and, for each captured second image, the corresponding position and/or orientation of the head of the wearer with respect to the second image-capturing device is determined.

As described with reference to step a), to this end it is possible to envision placing on the head of the wearer an accessory having set geometric characteristics. It may for example be a question of the chosen spectacle frame or of a frame other than that chosen, the latter preferably having dimensions larger than that chosen so that the gaze of the wearer is not constrained by the edges of the frame.

The frame is preferably equipped with a pinpointing system intended to allow the position of the head of the wearer in space to be determined from a captured image of the head of the wearer equipped with the locating system. This pinpointing system is described in detail in document FR2914173, page 7, line 5 to page 10, line 8. It will therefore not be described in more detail here.

This pinpointing system has predetermined geometric characteristics, which allow, from a captured image of the head of the wearer, in which image this locating system appears, the position and the orientation of the head of the wearer in space to be determined in the frame of reference associated with the image-capturing device. This pinpointing system therefore allows the position and orientation of the frame of reference associated with the head of the wearer to be determined in the frame of reference associated with the image-capturing device.

The head of the wearer may be directly equipped with the pinpointing system.

According to one variant of this third embodiment of step c), the series of second images of the head of the wearer being acquired while the wearer is fixating his gaze on a visual target, the position of this visual target with respect to the second image-capturing device is determined during the capture of each second image.

This may for example be done by virtue of a device, such as an eye tracker, for tracking gaze direction.

Such an eye tracker is for example integrated into certain cell phones and therefore easily accessible to most consumers.

A prior step of calibrating the eye tracker may be carried out at the opticians or in the home of the wearer.

As a variant, it is also possible to make provision for this target to have a known predetermined position with respect to the second image-capturing device used in step c). This is especially the case when this second image-capturing device is integrated into a display screen or at the very least has a fixed and predetermined position with respect to a display screen on which the target is displayed.

It is also possible, using instructions given to the wearer, to ask him to place the image-capturing device in a precise location, for example on the dashboard or television or screen looked at by the wearer.

Moreover, whatever the implemented embodiment of step c), the position and/or orientation in space of said second image-capturing device is preferably determined during the capture of said two- or three-dimensional second image, and information relating to the position and/or orientation of the head of the wearer in space during the capture of this second image is determined therefrom.

For this purpose, it is possible to make provision to carry out a step of calibrating the second device for capturing two- or three-dimensional images, in which step an image of a dedicated standard object is captured with this second image-capturing device.

This standard object is for example an image containing a test pattern, for example a black-and-white chequerboard of known dimensions. This standard object is placed at the working distance of the wearer, for example on the reading medium (book, computer screen, tablet, etc.) used by the wearer. An image of this standard object is captured using the second image-capturing device used by the wearer.

The standard object may be displayed by an application on a cell phone, especially on a smart phone. This cell phone may also be used to transmit the datasets and allow these datasets to be associated with the identifier of the wearer.

The application of this cell phone may especially be used to calibrate the WebCam of a computer by placing the telephone facing this WebCam. By placing the cell phone and computer "face to face" or rather "screen to screen", their respective video cameras may calibrate each other. The capturing devices of the computer and cell phone may recognize each other (brand and model).

It is also possible to determine the characteristics of a camera by photographing a test pattern that the application of the cell phone displays.

This allows, subsequently, by processing of this image of the standard object, the position and orientation of the second image-capturing device with respect to this standard object and therefore with respect to the reading medium to be determined.

Moreover, for each captured second image, information relating to the configuration of the second image-capturing device used in step c) are preferably recorded. It is for example a question of information giving the focal length of the objective of this device, the aperture, etc. Depending on information present in the captured second image, this information allows the distance between the wearer and the second image-capturing device at the moment of the capture of the second image in question, and/or the distance between the target and the second image-capturing device, to be determined.

Moreover, the second image-capturing device may include measuring means, such as for example a gyrometer, usually present in cell phones equipped with a camera, which may allow the orientation in space of the second image-capturing device to be determined. Measurements taken by these measuring means during the capture of an image are also recorded.

Generally, all the information relating to the capture of the second image is stored in association with this second image.

According to a fourth embodiment of step c), said dataset comprising said second representation of the head of the wearer, which representation is determined beforehand, is stored.

This dataset may especially contain the data corresponding to one or more three- or two-dimensional images captured beforehand. In the case of a plurality of two-dimensional images, the set may also contain in association with the data corresponding to each two-dimensional image, information relating to the position and/or orientation of the head of the wearer with respect to the second image-capturing device during the capture of this image.

In practice, as described above, step c) is carried out in a different place to step a).

Whatever the embodiment of step c), the dataset established in step c) is transmitted and stored in the information-processing server, which may optionally comprise the processing device T described above.

Preferably, in a step prior to step d), it is envisioned to transmit each two- or three-dimensional first image captured in step a) to an information-processing server and stored in correspondence with an identifier of the wearer. The identifier may be associated with the wearer or with the piece of equipment of the wearer. The expression "piece of equipment" is especially understood to mean an old or newly chosen frame.

After step b) has been carried out, the three determined particular points are also transmitted to the information-processing server and stored in correspondence with this identifier.

In the same way, each two- or three-dimensional second image captured in step c) is transmitted to an information-processing server and stored in correspondence with this identifier of the wearer.

Thus, each captured second image transmitted to the server may be associated with those particular points of the head of the wearer which were determined in step a), said image being stored on the server in correspondence with said identifier of the wearer.

Step d)

In step d), in said second representation of step b), the image of each of said particular points of the head of the wearer the relative positions in space of which were determined in step b) is identified.

It is then a question of performing an image recognition that may for example be carried out by virtue of a facial recognition algorithm, here an "Active Appearance Model" algorithm (see for example on this subject the article "*Active appearance models*", by T. F. Cootes, G. J. Edwards, C. J.

Taylor, in IEEE Transactions on Pattern Analysis and Machine Intelligence 23 (6): 681, 2011).

Step e)

In step e), information relating to the position and/or orientation of the head of the wearer during the determination of said second representation is deduced from this identification.

For this purpose, the position and/or orientation of the frame of reference associated with the head of the wearer and defined by the three particular points identified in step b) during the capture of the second images of the second representation or during the determination of the data contained in the corresponding set are/is sought.

Thus, in step e), said information relating to the position and/or orientation of the head of the wearer during the determination of said second representation are/is deduced from the identification carried out in step d) and the relative position in space of the three particular points of the head of the wearer determined in step b).

Generally, in step e), the position and/or orientation of the head of the wearer during the determination of said second representation, are/is determined as being the position and/or orientation of the head of the wearer for which the three particular points of the head of the wearer have the coordinates of the images of the three particular points identified in said second representation. It is a question of a calculation for optimizing the position and orientation of the frame of reference of the head of the wearer, which frame of reference is defined by the three particular points identified in step b).

In fact, it is a question of projecting the three-dimensional frame of reference of the head of the wearer determined in step b) into each second image, so as to determine the position and/or orientation of the head of the wearer at the moment of the capture of this second image in a frame of reference associated with the second image-capturing device.

The method called the "PostIt method" published by Daniel F. DeMenthon and Larry S. Davis in May 1995 may be used for this purpose. This method allows the position and/or orientation of an object to be found from a single two-dimensional image and a three-dimensional model of the object.

The implementation of this method requires at least 4 points of correspondence between the two-dimensional object and the three-dimensional model to be found.

The method may be divided into two steps. The first step corresponds to the projection of the three-dimensional model into the two-dimensional image and to the determination of a rotation matrix and a translation vector allowing the particular points of the model and the images of these particular points identified in the two-dimensional second images to be made to coincide.

The second step is an iteration step using a scaling factor to improve the precision of the projection carried out in the first step.

According to another simplified possibility, for example, in the case where:
- in step a), a series of first two-dimensional images is captured and, for each captured first image, the corresponding position and/or orientation of the head of the wearer with respect to the first image-capturing device are/is determined;
- in step c), using a second image-capturing device distinct from the first image-capturing device, at least one second two-dimensional image of the head of the wearer is captured constituting said second representation of the head of the wearer, then in step e), that first image of said series of first images which is closest said second image is associated with the second image captured in step c) and the position and/or orientation of the head of the wearer with respect to said second image-capturing device during the capture of said second image is identified with the position and/or orientation of the head of the wearer during the capture of this closest first image.

To do this, the mean of the Euclidean distances between the particular points of each first image of the series of first images and the corresponding particular points of the second image in question is determined.

That first image of the series of first images for which this mean is the lowest is associated with the second image captured in step c). Moreover, when the position and/or orientation of the second image-capturing device may be determined in an absolute frame of reference in space by virtue of measuring means integrated into the second image-capturing device (gyrometer), it is then possible to deduce the position and/or orientation of the head of the wearer in such an absolute frame of reference in space.

Step f)

In step f), from said second representation and the information deduced in step e), said behavioral parameter of the wearer is determined.

For this purpose, in the case where, in step c), a series of second images of the head of the wearer is acquired, in step f), said behavioral parameter of the wearer is determined depending on a statistical treatment of said second images of this series. It will be noted that this is possible by virtue of the construction of a frame of reference of the head of the wearer in step b) and of the subsequent determination of the position and/or orientation of the head of the wearer in step e); the determination of step f) is carried out while taking into account this position and/or this orientation.

For example, in the case where the wearer carries out step c) during a visual task of reading from a screen and by virtue of a second image-capturing device that is securely fastened to this screen, it is possible to determine, in step e), for each second image of the head of the wearer, the distance between the image-capturing device and the wearer. This distance may be considered identical to the reading distance when the image-capturing device is born by the reading medium.

It is also possible to deduce this reading distance from the second images captured in step c) and from the position and/or orientation of the head of the wearer determined in step e).

This may be done in various ways, either by processing images captured while the wearer is equipped with a pin-pointing system, or using data generated in a prior step of calibrating the second image-capturing device, or using information relating to the configuration (focal length in particular) of this second device during the image capture.

The reading distance may then be determined as an arithmetic mean of the reading distances determined for all or some of the second images of the series of second images.

The sought behavioral parameter may also comprise an eye-head coefficient equal to the ratio of the amplitude of the movement of an eye of the wearer in a determined direction to the maximum amplitude of the movement of this eye during a near-vision task, a reading task for example.

In this context, steps a) and b), which are carried out such as described above, serve to determine a reference posture of the wearer.

Steps c) to e) are also carried out as described above.

Furthermore, in step c), the wearer is placed in a situation in which he performs a predefined reading task.

This reading task involves reading at least one paragraph including a plurality of lines, for example 4 or 5 lines, from left to right or from right to left depending on the language in question.

It has been observed that the wearer adopts an increasingly natural position as he reads and especially when he changes page.

Therefore, preferably, a text including a plurality of pages is used, and more particularly the captured images corresponding to the last pages read are exploited.

The text is thus a target the position of which is known with respect to the medium at any given time. This position is therefore known in the frame of reference associated with the second image-capturing device, which is for example a smart phone.

In step c), an image of the head of the wearer is then captured, using the second image-capturing device, for various positions of the target corresponding to various gaze directions at the first working distance.

From these captured second images, the processing device of the information-processing server for example determines the position of the rotation center CRO of at least one eye of the wearer in the frame of reference associated with the head of the wearer. The principle of this determination is known per se and for example described in document FR2914173, an equivalent of which in English is the document US20100128220.

As a variant, the position of the eye rotation center in the frame of reference associated with the head of the wearer, the position of the pupil of the eye of the wearer and the radius of the eye of the wearer may be determined beforehand, for example by measurements taken by the optician.

They may be integrated into the dataset of said second images and constitute parameters for calibrating the second image-capturing device.

In step d) the image of each of said particular points of the head of the wearer, the relative positions in space of which were determined in step b), are identified in said second representation of step b), and in step e), information relating to the position and/or orientation of the head of the wearer during the determination of said second representation are deduced from this identification.

In practice, in step e), the posture of the head of the wearer is determined for each captured second image.

It is then possible to say that the direction of the gaze of the wearer in the frame of reference associated with the head of the wearer during each image capture is the straight line connecting this rotation center with the target in its corresponding position during the image capture.

The angular amplitude of the movement of the eyes of the wearer during the reading task is, in step f), from said second representation and the information deduced in step e), deduced therefrom as being the angular separation between the two gaze directions that are the furthest apart, in a given, especially horizontal or vertical, plane. This amounts to comparing all the postures of the head of the wearer in the captured second images to this reference.

Since the dimensions of the text displayed on the medium and read by the wearer, and the reading distance of the wearer, i.e. the distance between the eyes of the wearer and this text, are known, the maximum angular amplitude of the movement of each eye is then determined as being the angular extent of the text seen by the wearer, in the horizontal or vertical direction in question.

By dividing the angular amplitude of the movement of each eye by the maximum angular amplitude of the movement of each eye, a coefficient called the eye-head coefficient, which is characteristic of the behavior of the wearer during a reading task, is deduced therefrom.

This coefficient quantifies the propensity of the wearer to move his eyes or his head during the reading task. It is also possible to determine the average angular amplitude of the movement of the eye as being the average of the angular movements of the left eye and right eye of the wearer. It is then possible to deduce therefrom an average eye-head coefficient.

The static or dynamic posture adopted for the habitual activity in question for example corresponds to the orientation, i.e. the inclination, of the head with respect to an element associated with the activity in question of the wearer: reading medium, musical instrument, vehicle dashboard, etc.

The ergorama, associating with each direction of the gaze the distance between the eye and the point looked at, may be determined from gaze directions determined as described above, while varying the working distance, for example the reading distance, between two captures of a second image. A statistical treatment of the series of two- or three-dimensional second images captured also allows a quantity characterizing the variability in the aforementioned behavioral parameters to be deduced.

A small variance ensures that the behavioral parameter indeed characterizes the wearer. A high variance could mean that the wearer may be difficulty characterized by this parameter.

Thus, a behavioral parameter having a low variance will advantageously be taken into account when designing the ophthalmic lens intended for the wearer, whereas a behavioral parameter having a high variance will not be taken into account when designing the ophthalmic lens.

Lastly, the behavioral parameter determined may be the position of the spectacle frame of the wearer on his face.

Specifically, it is possible to determine the position of prominent points (constituted from the identified particular points) of the frame in the frame of reference of the head of the wearer. The position of the spectacle frame may thus be determined in this frame of reference of the head of the wearer.

This position may for example comprise a relative position of the frame temples and of the ears of the wearer and/or a position of the rims of the frame with respect to the pupils of the wearer and/or a position of the bridge of the frame with respect to the nose of the wearer. The position of the bridge of the frame may be determined in a vertical direction, corresponding to the height on the nose of the wearer, and depthwise, corresponding to a lens-eye distance.

The invention claimed is:

1. A method for determining at least one behavioral parameter of a wearer in order to design an ophthalmic lens for a spectacle frame of the wearer, the method comprising the following steps:
   a) acquiring a first dataset corresponding to a first representation of the head of the wearer in three dimensions;
   b) determining, from the first dataset, the relative position in space of at least three particular predefined morphological points of the face of the wearer;
   c) acquiring a second dataset corresponding to a second representation of the head of the wearer in a natural posture, comprising at least one image of each of the three particular predefined morphological points of the face of the wearer;
   d) identifying, in said second representation of step c), the image of each of said particular predefined morphological points of the face of the wearer, the relative positions in space of which were determined in step b);

e) deducing from identification information relating to the position and/or orientation of the head of the wearer during the determination of said second representation; and f) determining, from the information deduced in step e), said behavioral parameter of the wearer.

2. The method as claimed in claim 1, wherein, in step a), at least one three-dimensional image of the head of the wearer is acquired by virtue of a first device for capturing three-dimensional images, the three-dimensional image then constituting said first representation of the head of the wearer.

3. The method as claimed in claim 2, wherein, in step a), a series of three-dimensional first images of the head of the wearer is acquired and, in step b), said particular predefined morphological points are determined, by virtue of a statistical analysis, depending on the points of the head of the wearer, the relative positions of which are the most stable in the series of three-dimensional first images.

4. The method as claimed in claim 2, wherein, in step c), at least one three-dimensional second image of the head of the wearer is acquired by virtue of a second device configured to capture three-dimensional images, said three-dimensional second image constituting said second representation of the head of the wearer.

5. The method as claimed in claim 4, wherein, in step c), a series of three-dimensional second images of the head of the wearer is acquired, and in step f), said behavioral parameter of the wearer is determined depending on a statistical treatment of said second images of the series of three-dimensional second images.

6. The method as claimed in claim 5, wherein, in step c), the series of three-dimensional second images of the head of the wearer is acquired while the wearer is fixating the gaze of the wearer on a visual target, the position of the visual target with respect to the second image-capturing device being determined during the capture of each second image.

7. The method as claimed in claim 4, further comprising a step of calibrating the second device to capture three-dimensional images, in which step an image of a dedicated standard object is captured with the second image-capturing device.

8. The method as claimed in claim 4, wherein the position and/or orientation in space of said second image-capturing device is determined during the capture of said three-dimensional second image, and information relating to the position and/or orientation of the head of the wearer in space during the capture of the three-dimensional second image is determined therefrom.

9. The method as claimed in claim 4, wherein, in a step prior to step d), each three-dimensional second image captured in step b) is transmitted to an information-processing server and stored in correspondence with an identifier of the wearer.

10. The method as claimed in claim 4, wherein each captured second image transmitted to the server is associated with those particular predefined morphological points of the face of the wearer which were determined in step a), said image being stored on the server in correspondence with said identifier of the wearer.

11. The method as claimed in claim 1, wherein, in step a), a series of two-dimensional first images of the head of the wearer in various cephalic postures is acquired using a first device configured to capture two-dimensional images, the series of first images constituting said first representation of the head of the wearer, and for each captured first image, the corresponding position and/or orientation of the head of the wearer with respect to the first image-capturing device is determined.

12. The method as claimed in claim 11, wherein, in step c), at least one two-dimensional second image of the head of the wearer is captured using a second image-capturing device that is distinct from the first image-capturing device, said at least one two-dimensional second image of the head of the wearer constituting said second representation of the head of the wearer, and in step e), the first image of said series of first images which is closest said second image is associated with the second image captured in step c) and the position and/or orientation of the head of the wearer with respect to said second image-capturing device during the capture of said second image is identified with the position and/or orientation of the head of the wearer during the capture of the closest first image.

13. The method as claimed in claim 11, wherein, in step c), at least one two-dimensional second image of the head of the wearer is captured using a second image-capturing device, said at least one two-dimensional second image of the head of the wearer constituting said second representation of the head of the wearer.

14. The method as claimed in claim 13, wherein, in step c), a series of two-dimensional second images of the head of the wearer is acquired, and in step f), said behavioral parameter of the wearer is determined depending on a statistical treatment of said second images of the series of two-dimensional second images.

15. The method as claimed in claim 14, wherein, in step c), the series of two-dimensional second images of the head of the wearer is acquired while the wearer is fixating the gaze of the wearer on a visual target, the position of the visual target with respect to the second image-capturing device being determined during the capture of each second image.

16. The method as claimed in claim 13, further comprising a step of calibrating the second device to capture two-dimensional images, in which step an image of a dedicated standard object is captured with the second image-capturing device.

17. The method as claimed in claim 13, wherein the position and/or orientation in space of said second image-capturing device is determined during the capture of said two-dimensional second image, and information relating to the position and/or orientation of the head of the wearer in space during the capture of the two-dimensional second image is determined therefrom.

18. The method as claimed in claim 13, wherein, in a step prior to step d), each two-dimensional second image captured in step b) is transmitted to an information-processing server and stored in correspondence with an identifier of the wearer.

19. The method as claimed in claim 13, wherein each captured second image transmitted to the server is associated with the particular predefined morphological points of the face of the wearer which were determined in step a), said image being stored on the server in correspondence with said identifier of the wearer.

20. The method as claimed in claim 1, wherein, in step a) and/or in step c), said dataset comprising said first and second representations of the head of the wearer is stored, the first and second representations being determined beforehand.

21. The method as claimed in claim 1, wherein, in step c), the second representation of the head of the wearer is determined during one or more habitual activities of the wearer, in a user environment.

22. The method as claimed in claim 1, wherein, in step e), the position and/or orientation of the head of the wearer during the determination of said second representation determined computationally as being the position and/or orientation of the head of the wearer for which the three particular predefined morphological points of the face of the wearer have the coordinates of the images of the three particular predefined morphological points identified in said second representation.

23. The method as claimed in claim 1, wherein, in step a), a first representation of the head of the wearer is acquired by a person specialized in optometry, other than the wearer, and/or using a device dedicated to optometry, and in step c), a second representation of the head of the wearer is acquired under the responsibility of the wearer himself, without intervention of a person specialized in optometry and/or using a commonplace device.

* * * * *